United States Patent
Schulz et al.

(10) Patent No.: US 10,132,855 B2
(45) Date of Patent: Nov. 20, 2018

(54) METHOD AND DEVICE FOR MEASURING AND OPTIMIZING AN OPTOELECTRONIC COMPONENT

(71) Applicant: OSRAM Opto Semiconductors GmbH, Regensburg (DE)

(72) Inventors: Robert Schulz, Thalmassing (DE); Anton Vogl, Sinzing (DE); Raimund Oberschmid, Sinzing (DE); Roland Zeisel, Tegernheim (DE); Michael Dietz, Bamberg (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 220 days.

(21) Appl. No.: 14/769,788

(22) PCT Filed: Mar. 6, 2014

(86) PCT No.: PCT/EP2014/054364
§ 371 (c)(1),
(2) Date: Aug. 21, 2015

(87) PCT Pub. No.: WO2014/135644
PCT Pub. Date: Sep. 12, 2014

(65) Prior Publication Data
US 2016/0003890 A1   Jan. 7, 2016

(30) Foreign Application Priority Data
Mar. 8, 2013 (DE) .......... 10 2013 102 322

(51) Int. Cl.
*G01R 31/26* (2014.01)
*G01R 31/02* (2006.01)
*H05B 37/02* (2006.01)

(52) U.S. Cl.
CPC ....... *G01R 31/2635* (2013.01); *G01R 31/025* (2013.01); *H05B 37/0227* (2013.01); *G01N 2201/061* (2013.01)

(58) Field of Classification Search
CPC ...... G01R 31/02; G01R 31/26; G01R 31/025; G01R 31/2635; G01R 31/2637
(Continued)

(56) References Cited

U.S. PATENT DOCUMENTS

| 4,713,819 A | 12/1987 | Yoshikawa |
| 5,534,996 A | 7/1996 | Mori et al. |

(Continued)

FOREIGN PATENT DOCUMENTS

| CN | 2066992 U | 12/1990 |
| CN | 2757140 Y | 2/2006 |

(Continued)

OTHER PUBLICATIONS

Chen, Y.S., et al., "Study and Implementation of High Frequency Pulse LED Driver with Self-Oscillating Circuit," IEEE International Symposium on Circuits and Systems (ISCAS), May 15-18, 2011, pp. 498-501.

(Continued)

*Primary Examiner* — Chuong A Luu
(74) *Attorney, Agent, or Firm* — Slater Matsil, LLP

(57) ABSTRACT

A method can be used for measuring at least one optoelectronic component arranged on a connection carrier. The method includes exciting an electromagnetic oscillating circuit, which is formed by the optoelectronic component and the connection carrier, thus exciting the optoelectronic component in such a way that the optoelectronic component emits electromagnetic radiation, and measuring at least one electro-optical property of the optoelectronic component.

16 Claims, 4 Drawing Sheets

(58) Field of Classification Search
USPC .......................................................... 438/16
See application file for complete search history.

(56) References Cited

U.S. PATENT DOCUMENTS

| | | | |
|---|---|---|---|
| 6,946,858 | B2 | 9/2005 | Matsuyama |
| 8,102,119 | B2 | 1/2012 | Farquhar et al. |
| 8,159,257 | B2 | 4/2012 | Kato et al. |
| 8,803,541 | B2 | 8/2014 | Zudrell-Koch et al. |
| 2005/0085032 | A1 | 4/2005 | Aghababazadeh et al. |
| 2007/0131735 | A1 | 6/2007 | Michel et al. |
| 2007/0268038 | A1 | 11/2007 | Chiou |
| 2008/0018232 | A1* | 1/2008 | Zhang .................... B82Y 10/00 313/498 |
| 2008/0103706 | A1 | 5/2008 | Wu et al. |
| 2009/0039272 | A1* | 2/2009 | Krummacher ........ H01L 27/322 250/370.01 |
| 2012/0028375 | A1 | 2/2012 | Sato et al. |
| 2014/0312375 | A1* | 10/2014 | Schneider ............. H01L 33/505 257/98 |

FOREIGN PATENT DOCUMENTS

| | | |
|---|---|---|
| CN | 1867445 A | 11/2006 |
| CN | 200997713 Y | 12/2007 |
| CN | 102576820 A | 7/2012 |
| CN | 102621467 A | 8/2012 |
| CN | 202453465 U | 9/2012 |
| CN | 202471906 U | 10/2012 |
| DE | 3617588 A1 | 12/1986 |
| EP | 1777533 A1 | 4/2007 |
| GB | 1584370 A | 2/1981 |
| JP | S59174772 A | 10/1984 |
| JP | H02130942 A | 5/1990 |
| JP | 11233745 A | 8/1999 |
| JP | 200898539 A | 4/2008 |
| JP | 2008192874 A | 8/2008 |
| JP | 2011106882 A | 6/2011 |
| JP | 2011179937 A | 9/2011 |
| JP | 201295456 A | 5/2012 |
| JP | 2013500579 A | 1/2013 |
| JP | 2003188416 A | 7/2013 |
| WO | 2008120143 A2 | 10/2008 |
| WO | 2010034509 A2 | 4/2010 |

OTHER PUBLICATIONS

Harakawa, K., "Possibility of Wireless Power Supply by Electric Coupling Technology," Tanaka Technical Research Report, Partial Translation, 2010, 13 pages.

* cited by examiner

METHOD AND DEVICE FOR MEASURING AND OPTIMIZING AN OPTOELECTRONIC COMPONENT

This patent application is a national phase filing under section 371 of PCT/EP2014/054364, filed Mar. 6, 2014, which claims the priority of German patent application 10 2013 102 322.3, filed Mar. 8, 2013, each of which is incorporated herein by reference in its entirety.

TECHNICAL FIELD

A method and a device for measuring an optoelectronic component arranged on a connection carrier are specified. Furthermore, a method and a device for optimizing an optoelectronic component are specified.

BACKGROUND

In accordance with the prior art, electro-optical properties of optoelectronic components are usually measured by applying a DC voltage to the optoelectronic component. Occasionally, optoelectronic components are present at least temporarily in a form in which their connections are short-circuited, that is to say in which there is a negligible ohmic resistance between their connections. This is the case particularly if optoelectronic components are arranged on a connection carrier, for example, during the production of optoelectronic components. By way of example, optoelectronic components are mounted in a metallic leadframe, as a result of which the contacts of the optoelectronic components are short-circuited with respect to DC voltages. Consequently, these cannot be operated with DC current in order to determine their electro-optical properties for the purpose of process monitoring and/or process control.

While the optoelectronic components are singulated and provided with individually contactable connections at the end of the production process, it may be advantageous that the components are not yet singulated and/or not yet made individually contactable at least during substeps of the production process. However, it is desirable to be able to measure electro-optical properties of the optoelectronic components even in such a state, for example, in order to presort or to optimize the optoelectronic components and/or in order to adapt further production steps to the measured electro-optical properties. As a result, the rejects are reduced, thus affording a saving of time and costs.

In particular, the time required by the lengthy production steps such as the curing of a conversion material, for example, can be better utilized. During the production of light emitting diodes, for example, light emitting diodes which emit white light on the basis of volume conversion, the concentration and filling quantity of the conversion material are subject to fluctuations of varying magnitudes on account of current production methods. At the present time, in the manner of random sampling, an optoelectronic component is singulated and measured after the potting and baking of the material and can no longer be used for further production steps such as a plating step, for example.

It is known, for exciting optoelectronic components arranged on a connection carrier, to singulate the optoelectronic components at an early stage in the production process or at least to separate their short-circuited contacts and subsequently to make electrical contact with them. What is disadvantageous in this case is that separate contacts, in particular contacts protruding from the connection carrier and/or exposed contacts, can lead to mechanical problems, for example, instances of jamming and remain excluded from some production steps, for example, a plating step.

SUMMARY

Embodiments of the present invention specify a method and a device for measuring an optoelectronic component arranged on a connection carrier which are applicable if the optoelectronic component cannot be operated with DC voltage, particularly if there is a negligible ohmic resistance between the connections of the optoelectronic component. Further embodiments specify a method and a device for optimizing such an optoelectronic component arranged on a connection carrier.

In accordance with at least one embodiment of the method for measuring at least one optoelectronic component arranged on a connection carrier, the method comprises exciting at least one electromagnetic resonant circuit formed by the at least one optoelectronic component and the connection carrier, such that the at least one optoelectronic component is excited to emit electromagnetic radiation, and measuring at least one electro-optical property of the at least one optoelectronic component.

The invention is not restricted to exciting a single electromagnetic resonant circuit having a single optoelectronic component. Rather, the excited electromagnetic resonant circuit can also comprise two or more optoelectronic components whose electro-optical property can be measured. Moreover, a plurality of electromagnetic resonant circuits each having a single optoelectronic component or a plurality of electromagnetic resonant circuits each having a plurality of optoelectronic components can be excited. The electromagnetic resonant circuits can be independent of one another or else be coupled to one another. Moreover, it is not necessary for the electromagnetic resonant circuit or the electromagnetic resonant circuits to be excited in direct local proximity to the optoelectronic component or components. Rather, the regions of excitation and emission of electromagnetic radiation by the optoelectronic component(s) can also be spaced apart from one another. In this case, an optoelectronic component can be in particular an optoelectronic device or an element which is present as an optoelectronic device after further production steps have been performed. The optoelectronic component comprises at least one component part which can be excited to emit electromagnetic radiation.

What is achieved by virtue of the fact that the optoelectronic component is excited to emit electromagnetic radiation as a result of the excitation of an electromagnetic resonant circuit is that an electro-optical property of the optoelectronic component can be measured even if there is a negligible ohmic resistance, for example, an ohmic resistance in the micro-ohms range, between the connections of the optoelectronic component, such that the optoelectronic component is short-circuited. In particular, an electro-optical property of the optoelectronic component can be measured even if the optoelectronic component is short-circuited during at least part of the production process, for example, because it is arranged on a connection carrier and has not yet been singulated.

In accordance with at least one embodiment of the method, the optoelectronic component comprises a light emitting diode (LED), a laser diode, a semiconductor diode or a semiconductor chip. A laser diode is a semiconductor diode which emits laser radiation. Electromagnetic radiation is preferably emitted on the basis of electro-optical luminescence. An electromagnetic resonant circuit is an electrical circuit comprising inductive and/or capacitive elements. The total impedance of such an electrical circuit is generally complex-valued. In particular, an electromagnetic resonant circuit can comprise both inductive and capacitive elements. In this case, the absolute value of the total impedance assumes a minimum upon excitation with a specific frequency. The electromagnetic resonant circuit can preferably be excited with this specific frequency.

In accordance with at least one embodiment of the method, the optoelectronic component comprises a semiconductor layer sequence. The optoelectronic component preferably contains a III-V compound semiconductor material. III-V semiconductor materials are particularly suitable for generating radiation in the ultraviolet ($Al_x In_y Ga_{1-x-y} N$) through the visible ($Al_x In_y Ga_{1-x-y} N$, in particular for blue to green radiation, or $Al_x In_y Ga_{1-x-y} P$, in particular for yellow to red radiation) to the infrared ($Al_x In_y Ga_{1-x-y} As$) spectral range. In this context, $0 \leq x \leq 1$, $0 \leq y \leq 1$ and $x+y \leq 1$ in each case hold true, in particular where $x \neq 1$, $x \neq 1$, $x \neq 0$ and/or $y \neq 0$.

In accordance with at least one embodiment of the method, the connection carrier is a leadframe, in particular a metal frame. A multiplicity of optoelectronic components can be arranged on the connection carrier. The connection carrier can comprise at least one connection conductor region, wherein a respective optoelectronic component can be arranged in each connection conductor region. A connection conductor region is a region in which connection conductors are formed. In particular, connection conductors which can serve as connections for the electrical interconnection of the optoelectronic component during a process for manufacturing the optoelectronic component and/or after the completion of the optoelectronic component can be formed in the connection conductor region.

In accordance with at least one embodiment of the method, a respective interspace is formed between each two connection conductor regions. The connection carrier can furthermore comprise bridging regions, by which the connection conductor regions are conductively interconnected. A continuous connection carrier can be formed in a simplified manner by means of the bridging regions.

In accordance with at least one embodiment of the method, the at least one connection conductor region comprises at least one first connection region and a second connection region. A first connection of the optoelectronic component can be conductively connected to the first connection region, and a second connection of the optoelectronic component can be conductively connected to the second connection region. The first connection can be conductively connected to the first connection region by direct electrical contact, and the second connection can be conductively connected to the second connection region by means of a bonding wire. The first connection region and the second connection region can be conductively connected to one another by the connection carrier.

In accordance with at least one embodiment of the method, the electromagnetic resonant circuit is formed by the optoelectronic component, the first connection region, the second connection region and also the conductive connection between the first connection region and the second connection region. The conductive connection between the first connection region and the second connection region can at least partly enclose a non-conductive interspace. As a result, the inductance and capacitance present in the surroundings of the interspace are utilized for the electromagnetic resonant circuit. The interspace is preferably free of solid matter. What is achieved as a result is that a means for exciting the electromagnetic resonant circuit, for example, an inductive element or a ferrite core, can be introduced into the interspace, as a result of which a more effective excitation of the electromagnetic resonant circuit can be achieved.

In accordance with at least one embodiment of the method, the electro-optical property of the optoelectronic component is the brightness, the color locus or the spectrum of the electromagnetic radiation emitted by the optoelectronic component. Further properties of the optoelectronic component can be determined on the basis of the measured electro-optical property. By way of example, it is possible to determine at least one lifetime of at least one type of charge carriers in the optoelectronic component or in at least one part of the optoelectronic component.

In accordance with at least one embodiment of the method, exciting the electromagnetic resonant circuit comprises applying an electrical voltage to two electrical contacts in the electromagnetic resonant circuit, in particular to two contact points on the connection carrier. Optionally or additionally, exciting the electromagnetic resonant circuit comprises inducing an electrical AC voltage in the electromagnetic resonant circuit by generating a temporally variable alternating electromagnetic field. The inductive excitation has the advantage that the excitation can be effected contactlessly. The temporally variable alternating electromagnetic field can be generated by an inductive element, in particular a coil having one or a plurality of turns. The inductive element can be arranged above or below, i.e., on both sides of, the connection carrier. The distance between the connection carrier and the inductive element can also vary, but is preferably kept constant. By way of example, the inductive element can be led at a constant distance from the connection carrier over regions of different optoelectronic components.

Preferably, the inductive element has similar dimensions and/or a similar shape to the electromagnetic resonant circuit. What is achieved by the locally delimited excitation of the electromagnetic resonant circuit is that an electro-optical property of an individual optoelectronic component can be measured, without adjacent optoelectronic components that are arranged on the same connection carrier, for example, likewise being excited to emit electromagnetic radiation.

However, the inductive element can also have, for example, smaller dimensions than the electromagnetic resonant circuit or the simultaneously formed resonant circuits. As a result, it is also possible to measure an electro-optical property of a plurality of (for example, adjacent) optoelectronic components which are excited simultaneously to emit electromagnetic radiation.

As described above, the regions of excitation and emission of electromagnetic radiation by the optoelectronic component(s) can be spaced apart from one another. Depending on the geometry of the connection carrier and of the optoelectronic components arranged thereon, on the one hand, and the spatial distribution of the magnetic field strength, on the other hand, a plurality of optoelectronic components can be excited to emit electromagnetic radiation, wherein the intensity of the respectively emitted radiation can vary greatly between the optoelectronic components.

In accordance with at least one embodiment of the method, the inductive element at least partly encloses a ferromagnetic element extending from the inductive element in the direction of the electromagnetic resonant circuit. What is achieved as a result is that the magnetic field lines diverge to a lesser extent and as a result are concentrated to a greater extent in the region of the electromagnetic resonant circuit.

The ferromagnetic element can be a ferrite core, for example. Preferably, the inductive element and/or the ferromagnetic element at least partly penetrate(s) the electromagnetic resonant circuit during the excitation. A particularly strong magnetic coupling between the inductive element and the electromagnetic resonant circuit is achieved as a result.

In accordance with at least one embodiment of the method, an AC voltage is applied to the electrical contacts in the electromagnetic resonant circuit and/or to the inductive element. The AC voltage is preferably a radio-frequency voltage. The radio-frequency voltage is preferably applied via a matching circuit that serves for impedance matching. The frequency of the radio-frequency voltage is preferably 1 MHz to 10 GHz, particularly preferably 10 MHz to 1 GHz, and particularly preferably 25 MHz to 500 MHz. Preferably, the frequency of the radio-frequency voltage is at or near a resonant frequency of the electromagnetic resonant circuit. The power applied for the excitation can be between 1 watt and 100 watts, for example. Preferably, the method comprises setting the frequency of the radio-frequency voltage. Setting the frequency of the radio-frequency voltage can comprise closed-loop control on the basis of a measurement of the intensity of the electromagnetic radiation emitted by the optoelectronic component. Preferably, the imaginary part of the effective impedance of the conductive connection between the first connection region and the second connection region at the frequency of the radio-frequency voltage is greater than the real part of the effective impedance, particularly preferably ten times greater and particularly preferably one hundred times greater.

What is achieved by virtue of the fact that the electromagnetic resonant circuit is excited by means of an AC voltage is that the optoelectronic component can be measured, without interrupting the conductive connection between its connections, which would cause a short circuit upon a DC voltage being applied. What is achieved by virtue of the fact that the AC voltage is coupled locally into the electromagnetic resonant circuit is that an individual optoelectronic component can be measured, without other optoelectronic components, in particular optoelectronic components that are adjacent on the connection carrier, being excited at the same time. That is the case particularly if the connection carrier comprises a plurality of connection conductor regions with a plurality of optoelectronic components and the connection conductor regions are conductively connected to one another in each case by bridging regions.

The invention furthermore relates to a method for optimizing an optoelectronic component. In accordance with at least one embodiment, the method comprises performing a method according to the invention for measuring an optoelectronic component, comparing the at least one measured electro-optical property of the optoelectronic component with a desired value, and modifying the optoelectronic component on the basis of the comparison. Modifying can comprise, in particular, adapting the electro-optical property to the desired value. Optionally or additionally, the method can comprise sorting optoelectronic components on the basis of the measured electro-optical property.

Optionally or additionally, the method can furthermore comprise adapting a production step on the basis of the comparison of the measured electro-optical property with the desired value. The production step can be, in particular, applying a conversion material to an LED, in particular a white light generating LED. The LED can comprise, for example, a housing, a blue semiconductor chip, a conversion material and, if appropriate, further potting materials.

In this case, the electro-optical property of the optoelectronic component is preferably the color locus of the electromagnetic radiation emitted by the optoelectronic component. Preferably, when the conversion material is applied, the quantity of the conversion material and/or the concentration of a conversion substance contained therein are/is adapted depending on the measured color locus in order to achieve desired color properties of the finished LED and/or to realize a narrower color distribution. Although the spectrum of the electromagnetic radiation emitted by an LED has a slight temperature dependence and the LED heats up on account of the excitation with a radio-frequency voltage, the color locus can be determined sufficiently accurately by the method according to the invention. After the conversion material has been applied, the optoelectronic component can be provided, for example, with a housing or an optical element. If a plurality of optoelectronic components are arranged on the connection carrier, then the assemblage comprising connection carrier and optoelectronic components can subsequently be singulated. In this case, the common connection carrier is divided into a plurality of connection carriers, such that the finished optoelectronic components each have a connection carrier.

The invention furthermore relates to a device for measuring an optoelectronic component. In accordance with at least one embodiment, the device comprises a connection carrier, on which at least one optoelectronic component can be arranged, a radio-frequency generator, a matching circuit, means for exciting an electromagnetic resonant circuit comprising the connection carrier and the at least one optoelectronic component, and a measuring device designed to measure at least one electro-optical property of the optoelectronic component. The electromagnetic resonant circuit can be excited, for example, inductively and thus contactlessly or via electrical contacts.

The invention furthermore relates to a device for optimizing an optoelectronic component. In accordance with at least one embodiment, the device comprises a device according to the invention for measuring an optoelectronic component, a control unit designed to compare the measured electro-optical property of the optoelectronic component with a desired value, and means for modifying the optoelectronic component on the basis of the comparison. The means for modifying the optoelectronic component on the basis of the comparison can comprise means for adapting the electro-optical property to the desired value. Optionally, or additionally, the means for modifying the optoelectronic component on the basis of the comparison can comprise means for adapting a production step on the basis of the comparison. Preferably, the control unit is designed to control the means for modifying the optoelectronic component on the basis of the measured electro-optical property and/or on the basis of the comparison of the measured electro-optical property with the desired value.

BRIEF DESCRIPTION OF THE DRAWINGS

The described devices are particularly suitable for performing the methods described further above. Features explained in association with the method can therefore also be used for the devices, and vice versa.

Further advantages, advantageous embodiments and developments will become apparent from the exemplary embodiments described below in association with the figures.

In the figures:

FIG. 1 shows a plan view of a first exemplary embodiment of a connection carrier to which the method according to the invention is applicable;

FIG. 2 shows a plan view of a second exemplary embodiment of a connection carrier to which the method according to the invention is applicable;

FIG. 3 shows a block diagram of an excitation circuit with an electromagnetic resonant circuit to be excited;

FIG. 4 shows a first exemplary embodiment of the coupling-in device of the excitation circuit illustrated in FIG. 3;

FIG. 5 shows a second exemplary embodiment of the coupling-in device of the excitation circuit illustrated in FIG. 3;

FIG. 6 shows a third exemplary embodiment of the coupling-in device of the excitation circuit illustrated in FIG. 3;

FIG. 7 shows a detail view of the first exemplary embodiment of a connection carrier in connection with the first exemplary embodiment of the coupling-in device of the excitation circuit illustrated in FIG. 3; and FIG. 8 shows an electromagnetic spectrum measured according to the invention of an optoelectronic component.

Figure 1:
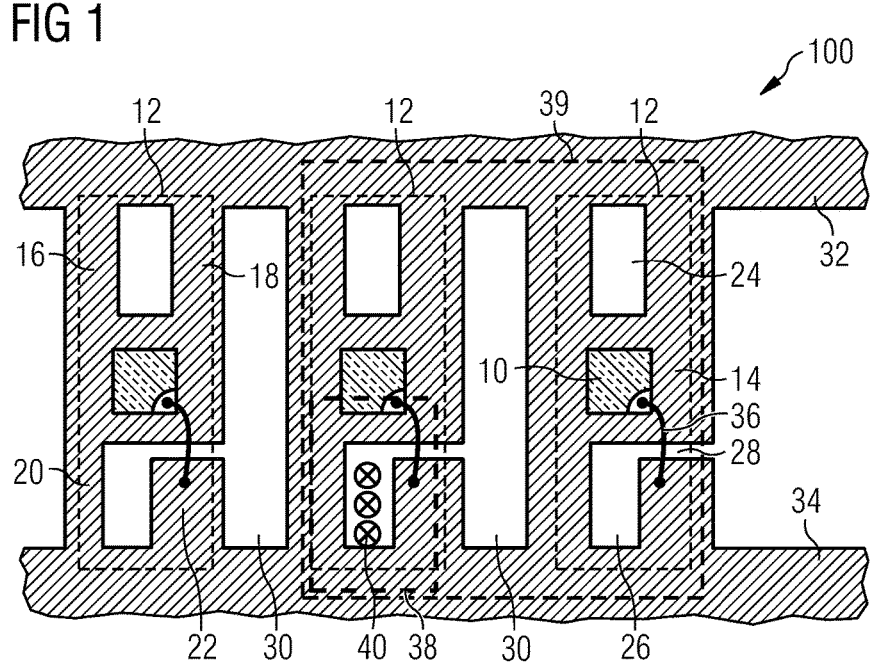

Elements that are identical, of identical type of act identically are provided with the same reference signs in the figures. The figures and the size relationships of the elements illustrated in the figures among one another should not be regarded as to scale. Rather, individual elements may be illustrated with exaggerated size in order to enable better illustration and/or in order to afford a better understanding.

A cross enclosed by a circle in a drawing indicates a magnetic field which is directed into the plane of the drawing at a specific point in time. However, the magnetic fields used in the present case are temporally variable, and a magnetic field directed into the plane of the drawing at one specific point in time can be directed out of the plane of the drawing at another point in time. Only the crucially involved magnetic field lines are illustrated.

DETAILED DESCRIPTION OF ILLUSTRATIVE EMBODIMENTS

FIG. 1 shows a plan view of a first exemplary embodiment—designated overall by 100—of a connection carrier to which the method according to the invention is applicable. Optoelectronic components 10 are arranged on the connection carrier 100, which consists of metal, for example. The connection carrier 100 comprises three connection conductor regions 12, which are arranged at regular distances from one another and each have the same structure and alignment. Each of the connection conductor regions 12 comprises a central region 14 and first to fourth connection conductors 16, 18, 20, 22, each having the same width, wherein in each case the first connection conductor 16 and the second connection conductor 18 are arranged on a first side of the central region 14 and the third connection conductor 20 and the fourth connection conductor 22 are arranged on a second side of the central region 14, the second side being situated opposite the first side. There is in each case a first interspace 24 between the first and second connection conductors 16, 18 on the first side of the central region 14, and there is in each case a second interspace 26, having the same width as the first interspace 24, between the third and fourth connection conductors 20, 22 on the second side of the central region 14. Furthermore, in each connection conductor region 12, in each case the fourth connection conductor 22 on the second side of the central region 14 is separated from the central region 14 by a third interspace 28; the first to third connection conductors 16, 18, 20 in each case directly adjoin the central region 14.

The connection conductor regions 12 are separated from one another overall by fourth interspaces 30. The width of the third interspaces 28 is less than the width of the first and second interspaces 24, 26, and the width of the first and second interspaces 24, 26 is less than the width of the fourth interspaces 30. The connection carrier 100 furthermore comprises a first bridging region 32 and a second bridging region 34, which are arranged on opposite sides of the connection conductor regions 12. In each connection conductor region 12, in each case the first and second connection conductors 16, 18 on the first side of the central region 14 are connected to the first bridging region 32, and the third and fourth connection conductors 20, 22 on the second side of the central region 14 are connected to the second bridging region 34. The first and second bridging regions 32, 34 thus form a conductive connection between the connection conductor regions 12.

A respective optoelectronic component 10 is arranged on the central region 14 of each connection conductor region 12, one connection of the optoelectronic component being in direct electrical contact with the central region 14. The central region 14 thus acts as a first connection region for the connection of the optoelectronic component 10. A second connection of the optoelectronic component 10 is connected to the fourth connection conductor 22 in each case by a bonding wire 36 across the third interspace 28. The fourth connection conductor 22 thus acts as a second connection region for the connection of the optoelectronic component 10. Consequently, the optoelectronic component 10, the bonding wire 36, the fourth connection conductor 22, a part of the second bridging region 34, the third connection conductor 20 and a part of the central region 14 in each case form an electromagnetic resonant circuit 38. By virtue of the fact that the electromagnetic resonant circuit 38 is formed around the second interspace 26, the inductance and capacitance present in the surroundings of the second interspace 26 are utilized for the electromagnetic resonant circuit 38. An electrical AC voltage can be induced in the electromagnetic resonant circuit 38 by means of a temporally variable magnetic field 40 present in the second interspace 26.

FIG. 1 additionally depicts purely by way of example a second electromagnetic resonant circuit 39, which is formed by a further region of the connection carrier 100 that includes two adjacent optoelectronic components 10. This is intended to make it clear that depending on the geometry of the connection carrier 100 and the optoelectronic components 10 arranged thereon, on the one hand, and the spatial distribution of the magnetic field strength and also the frequency of the alternating field, on the other hand, a plurality of optoelectronic components 10 can be excited to emit electromagnetic radiation. In this case, the intensity of the respectively emitted radiation can vary greatly between the optoelectronic components 10. By way of example, the electromagnetic resonant circuit 39 can be formed by a plurality of connection conductors and parts of the bridging regions. In a manner similar to that in the case of the electromagnetic resonant circuit 38, the inductance and capacitance present in the (further) surroundings of the second interspace 26 are utilized for the electromagnetic resonant circuit 39. An electrical AC voltage can in turn be induced in the electromagnetic resonant circuit 39 by means of a temporally variable magnetic field 40 present in the second interspace 26. The two included adjacent optoelectronic components 10 can thereby be excited to emit electromagnetic radiation.

Figure 2:
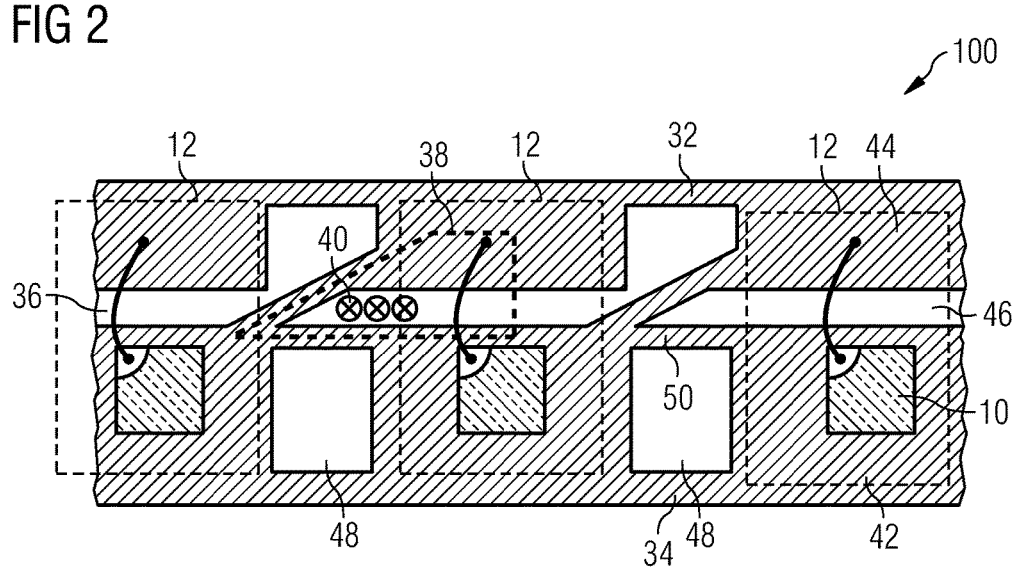

FIG. 2 shows a plan view of a second exemplary embodiment—designated overall by 100—of a connection carrier to which the method according to the invention is applicable. Optoelectronic components 10 are once again arranged on the connection carrier 100, which likewise consists of metal, for example. The connection carrier 100 also comprises three connection conductor regions 12, which are arranged at regular distances from one another and each have the same structure and alignment. Each of the connection conductor regions 12 comprises a first connection conductor 42 and a second connection conductor 44, each having the same width. There is in each case a first interspace 46 between the first and second connection conductors 42, 44.

The connection conductor regions 12 are separated from one another overall by second interspaces 48. The width of the first interspaces 46 is less than the width of the second interspaces 48. The connection carrier 100 furthermore comprises a first bridging region 32 and a second bridging region 34, which are arranged on opposite sides of the connection conductor regions 12. In each connection conductor region 12, in each case the first connection conductor 42 is connected to the second bridging region 34, and the second connection conductor 44 is connected to the first bridging region 32. The bridging regions 32, 34 thus form a conductive connection between the connection conductor regions 12.

The connection carrier 100 furthermore comprises third bridging regions 50, which in each case across one of the second interspaces 48 both connect the first connection conductors 42 of two adjacent connection conductor regions 12 to one another and connect the first and second connection conductors 42 and 44 of one of the two adjacent connection conductor regions 12 to one another. Consequently, the third bridging regions 50 also form a conductive connection between the connection conductor regions 12.

A respective optoelectronic component 10 is arranged on the first connection conductor 42 of each connection conductor region 12, one connection of the optoelectronic component being in direct electrical contact with the first connection conductor 42. The first connection conductor 42 thus acts as a first connection region for the connection of the optoelectronic component 10. A second connection of the optoelectronic component 10 is connected to the second connection conductor 44 in each case by a bonding wire 36 across the first interspace 46. The second connection conductor 44 thus acts as a second connection region for the connection of the optoelectronic component 10. Consequently, the optoelectronic component 10, a part of the first connection conductor 42, the third bridging region 50, a part of the second connection conductor 44 and the bonding wire 36 in each case form an electromagnetic resonant circuit 38. By virtue of the fact that the electromagnetic resonant circuit 38 is formed around the first interspace 46, the inductance and capacitance present in the surroundings of the first interspace 46 are utilized for the electromagnetic resonant circuit 38. An electrical AC voltage can in turn be induced in the electromagnetic resonant circuit 38 by means of a temporally variable magnetic field 40 present in the first interspace 46.

Figure 3:
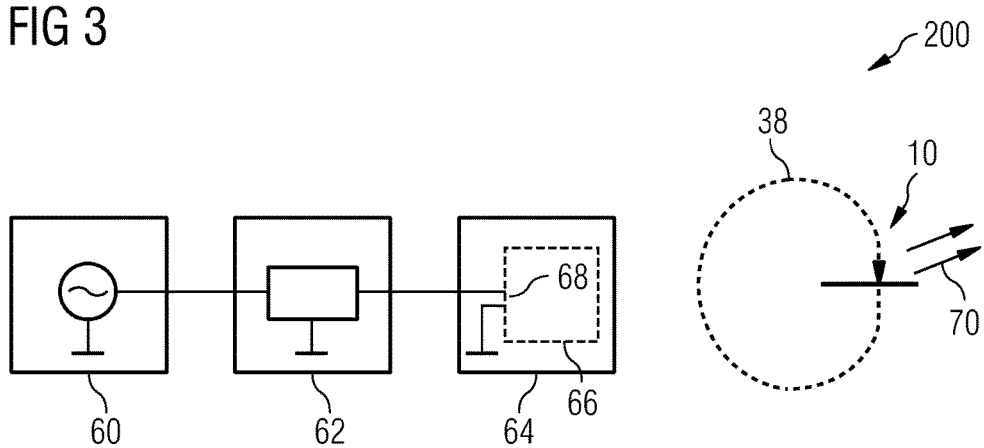

FIG. 3 shows a block diagram of an excitation circuit—designated overall by 200—with an electromagnetic resonant circuit 38 to be excited. The electromagnetic resonant circuit 38, which is illustrated schematically here, can be, for example, the electromagnetic resonant circuit 38 illustrated in FIG. 1 or the electromagnetic resonant circuit 38 illustrated in FIG. 2. The excitation circuit 200 comprises a radio-frequency generator 60 designed to generate a radio-frequency voltage. The voltage generated by the radio-frequency generator 60 is applied to a circuit element 64 via a matching circuit 62. The matching circuit 62 serves for impedance matching between the radio-frequency generator 60 and the circuit element 64. The circuit element 64 comprises a coupling-in device 66 having two connections 68. As explained in greater detail below, the coupling-in device 66 can be an inductive coupling-in device or a coupling-in device via electrical contacts. The electromagnetic resonant circuit 38 is excited by the excitation of the coupling-in device 66 with a radio-frequency voltage. The electromagnetic resonant circuit 38 comprises an optoelectronic component 10, illustrated schematically here, through which current flows upon excitation of the electromagnetic resonant circuit 38 and which therefore emits electromagnetic radiation 70.

Figure 4:
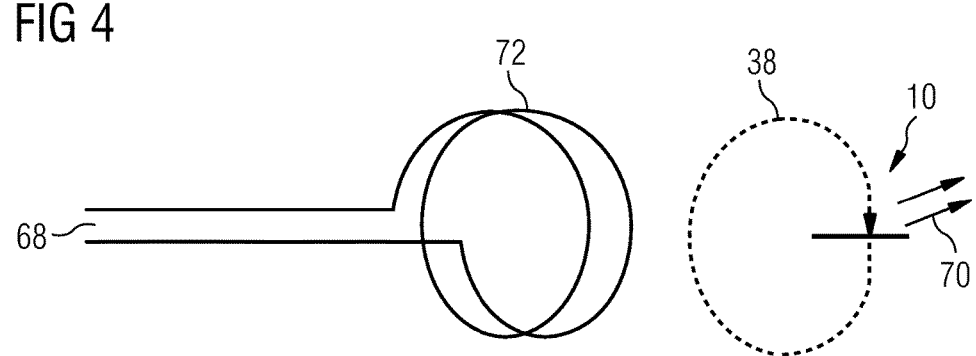

FIG. 4 shows a first exemplary embodiment of the coupling-in device 66 of the excitation circuit 200 illustrated in FIG. 3. A coil 72 acting as an inductive element is arranged between the two connections 68. The coil 72 can have one or a plurality of turns. The coil 72 is arranged in proximity to the electromagnetic resonant circuit 38, illustrated schematically here, as a result of which there is an inductive coupling between the coil 72 and the electromagnetic resonant circuit 38. A temporally variable magnetic field (not shown here) generated by excitation of the coil 72 with a radio-frequency voltage therefore induces an electrical AC voltage in the electromagnetic resonant circuit 38, which voltage excites the electromagnetic resonant circuit 38 to oscillate. Optionally, the coil 72 can be introduced into the electromagnetic resonant circuit 38 for the purpose of better inductive coupling. By way of example, the coil 72 can be introduced into the second interspace 26 of the first exemplary embodiment of a connection carrier or into the first interspace 46 of the second exemplary embodiment of a connection carrier. The electromagnetic resonant circuit 38 can be excited contactlessly by means of the coil 72.

Figure 5:
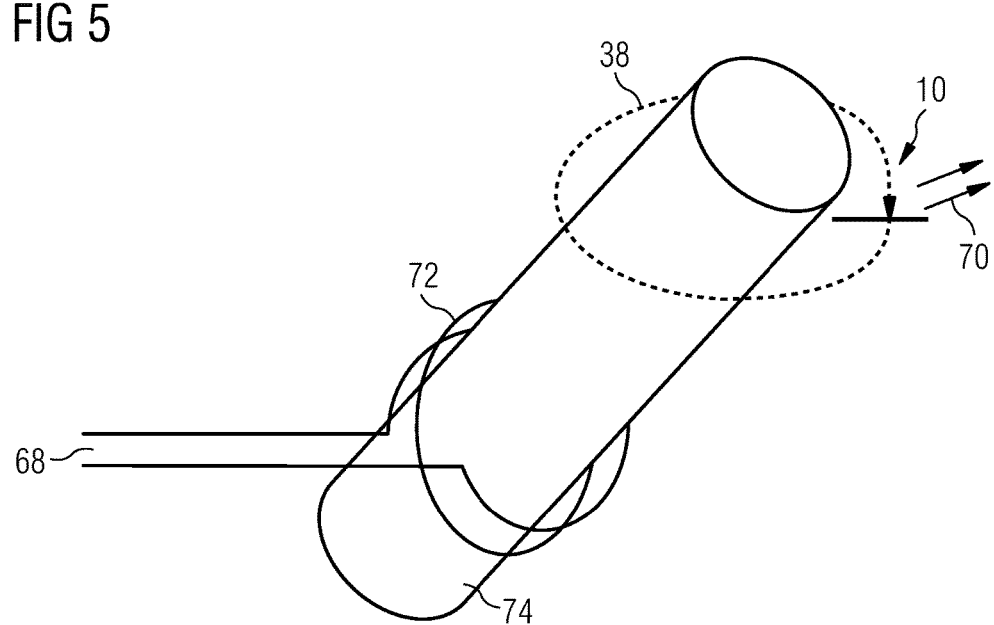

FIG. 5 shows a second exemplary embodiment of the coupling-in device 66 of the excitation circuit 200 illustrated in FIG. 3. As in the first exemplary embodiment of the coupling-in device 66 of the excitation circuit 200 illustrated in FIG. 3, a coil 72 acting as an inductive element is arranged between the two connections 68. The coil 72 can have one or a plurality of turns. The coil 72 encloses a ferrite core 74 acting as a ferromagnetic element. The temporally variable magnetic field (not shown here) generated by the coil 72 is concentrated by the ferrite core 74, such that the magnetic field lines do not diverge in proximity to the coil, but rather are guided substantially parallel into the region in which the electromagnetic resonant circuit 38, illustrated schematically here, is arranged. The ferrite core 74 is arranged in proximity to the electromagnetic resonant circuit 38. Optionally, the ferrite core 74 can be introduced into the electromagnetic resonant circuit 38 for the purpose of better inductive coupling. The ferrite core 74 can also be introduced, for example, into the second interspace 26 of the first exemplary embodiment of a connection carrier or into the first interspace 46 of the second exemplary embodiment of a connection carrier. The electromagnetic resonant circuit 38 can likewise be excited contactlessly by means of the ferrite core 74.

Figure 6:
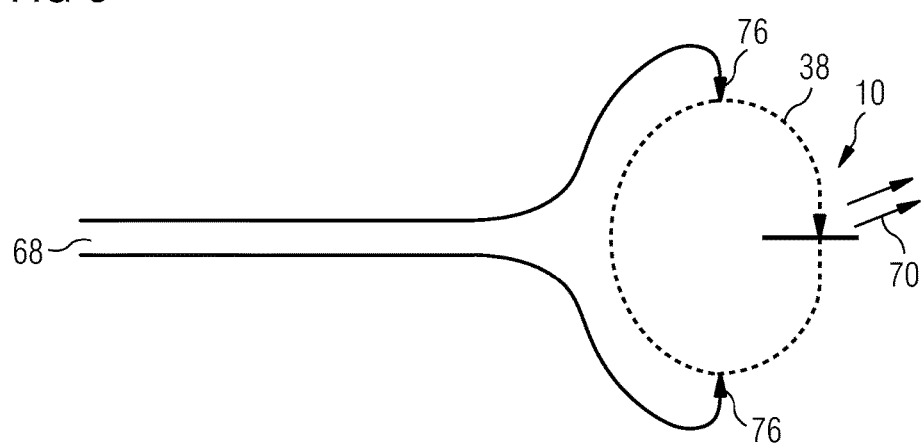

FIG. 6 shows a third exemplary embodiment of the coupling-in device 66 of the excitation circuit 200 illustrated in FIG. 3. In this exemplary embodiment, the electromagnetic resonant circuit 38, illustrated schematically here, is excited directly via two electrical contacts 76. The radio-frequency voltage present at the two connections 68 is coupled directly into the electromagnetic resonant circuit 38 via the electrical contacts 76.

Figure 7:
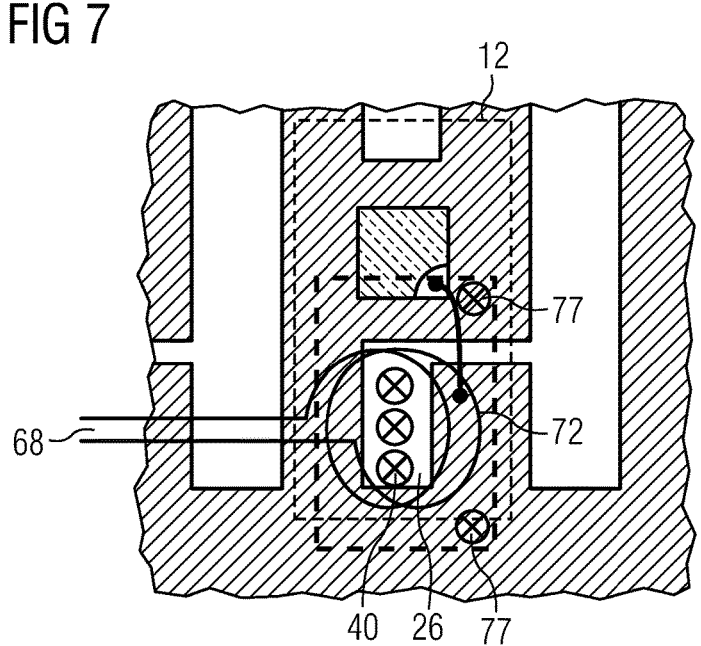

FIG. 7 shows a detail view of the first exemplary embodiment of a connection carrier in connection with the first exemplary embodiment of the coupling-in device of the excitation circuit illustrated in FIG. 3. The coil 72 excited with a radio-frequency voltage via the connections 68 is arranged in direct proximity to the second interspace 26 and generates a temporally variable magnetic field 40 therein. On account of this arrangement, there is a strong inductive coupling between the coil 72 and the electromagnetic resonant circuit (not shown here).

FIG. 7 illustrates by way of example a combination of the first exemplary embodiment of a connection carrier with the first exemplary embodiment of the coupling-in device of the excitation circuit illustrated in FIG. 3. However, the invention is not restricted to this combination; in particular, each of the first and second exemplary embodiments of a connection carrier can be combined with each of the first to third exemplary embodiments of the coupling-in device of the excitation circuit illustrated in FIG. 3. By way of example, the two electrical contacts 76 of the coupling-in device 66 shown in FIG. 6, which are preferably embodied as needle points, can be placed onto the connection carrier 100 at the positions designated by the reference sign 77 in FIG. 7, in order to excite the electromagnetic resonant circuit 38.

Figure 8:
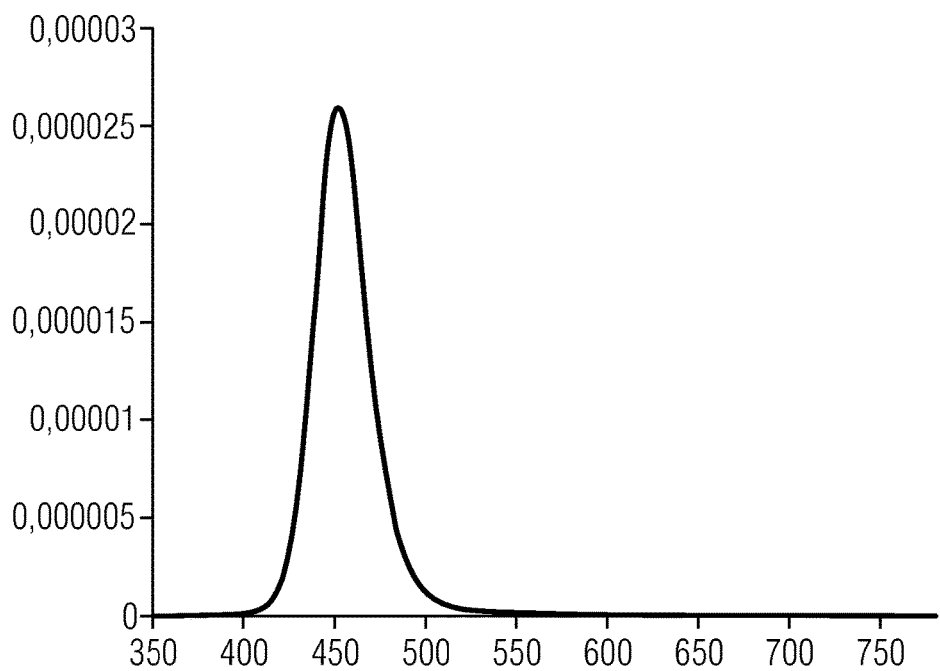

FIG. 8 shows a spectrum of the electromagnetic radiation emitted by an optoelectronic component, the spectrum being measured according to the invention. In this case, the electromagnetic resonant circuit was excited contactlessly. The optoelectronic component is a light emitting diode (power top LED) which predominantly emits electromagnetic radiation in the visible range of the electromagnetic spectrum and in particular predominantly blue light. In the drawing, the measured intensity of the electromagnetic radiation in arbitrary units is plotted against the wavelength of the electromagnetic radiation in nanometers. The spectrum of the electromagnetic radiation emitted by the optoelectronic component substantially corresponds to the spectrum which would be measurable in the case of a singulated optoelectronic component being excited with a DC voltage. On account of the heating of the optoelectronic component as a result of the excitation with a radio-frequency voltage, the spectrum is slightly shifted; however, an electro-optical property such as, for example, the color locus of the optoelectronic component can be determined reliably from the measured spectrum.

The invention is not restricted to the exemplary embodiments by the description on the basis of the exemplary embodiments. Rather, the invention encompasses any novel feature and also any combination of features, which in particular includes any combination of features in the patent claims, even if this feature or this combination itself is not explicitly specified in the patent claims or exemplary embodiments.

The invention claimed is:

1. A method for measuring a property of an optoelectronic component arranged on a connection carrier, the method comprising:
   exciting an electromagnetic resonant circuit formed by the optoelectronic component and the connection carrier, such that the optoelectronic component is excited to emit electromagnetic radiation; and
   measuring an electro-optical property of the optoelectronic component.

2. The method according to claim 1, wherein the connection carrier comprises a connection conductor region, wherein the optoelectronic component is arranged in the connection conductor region.

3. The method according to claim 2, wherein the connection carrier comprises a plurality of connection conductor regions, a respective interspace is formed between each two adjacent connection conductor regions and wherein the connection carrier comprises a bridging region, by which the connection conductor regions are conductively interconnected.

4. The method according to claim 2, wherein the connection carrier further comprises a second connection region, wherein a first connection of the optoelectronic component is conductively connected to the connection region, a second connection of the optoelectronic component is conductively connected to the second connection region, and the connection region and the second connection region are conductively connected to one another by the connection carrier.

5. The method according to claim 4, wherein the electromagnetic resonant circuit is formed by the optoelectronic component, the connection region, the second connection region and the conductive connection between the connection region and the second connection region.

6. The method according to claim 4, wherein the conductive connection between the connection region and the second connection region at least partly encloses a non-conductive interspace.

7. The method according to claim 1, wherein the electro-optical property of the optoelectronic component is a brightness, a color locus or a spectrum of electromagnetic radiation emitted by the optoelectronic component.

8. The method according to claim 1, wherein exciting the electromagnetic resonant circuit comprises applying an electrical voltage to two electrical contacts in the electromagnetic resonant circuit.

9. The method according to claim 1, wherein exciting the electromagnetic resonant circuit comprises inducing an electrical AC voltage in the electromagnetic resonant circuit by generating a temporally variable alternating electromagnetic field.

10. The method according to claim 9, wherein the temporally variable alternating electromagnetic field is generated by an inductive element.

11. The method according to claim 10, wherein the inductive element at least partly encloses a ferromagnetic element extending from the inductive element in the direction of the electromagnetic resonant circuit.

12. The method according to claim 1, wherein the optoelectronic component is excited to emit electromagnetic radiation on the basis of electro-optical luminescence.

13. A method for operating an optoelectronic component, the method comprising:
   exciting an electromagnetic resonant circuit formed by the optoelectronic component and a carrier on which the optoelectronic component is arranged, such that the optoelectronic component is excited to emit electromagnetic radiation;
   measuring an electro-optical property of the optoelectronic component;
   comparing the measured electro-optical property of the optoelectronic component with a desired value; and
   modifying the optoelectronic component based on the comparing.

14. The method according to claim 13, wherein, when a conversion material is applied to the optoelectronic component, a quantity of the conversion material or a concentration of a conversion substance contained therein is adapted on the basis of a comparison of a measured color locus with a desired value of color locus.

15. A device, the device comprising:
- a connection carrier, on which an optoelectronic component can be arranged;
- a radio-frequency generator;
- a matching circuit;
- an excitation circuit configured to excite an electromagnetic resonant circuit comprising the connection carrier and the optoelectronic component; and
- a measuring device configured to measure an electro-optical property of the optoelectronic component.

16. The device according to claim 15, further comprising:
- a controller configured to compare the measured electro-optical property of the optoelectronic component with a desired value; and
- means for modifying the optoelectronic component on the basis of the comparison.

* * * * *